(12) United States Patent
Chevallet et al.

(10) Patent No.: US 7,891,625 B2
(45) Date of Patent: Feb. 22, 2011

(54) MEDICAL MACHINE COMPRISING A SUSPENSION MEANS FOR SUSPENDING LIQUID BAGS

(75) Inventors: Jacques Chevallet, Serezin du Rhone (FR); Eric Dejaiffe, Francheville (FR)

(73) Assignee: Gambro Lundia AB, Lund (SE)

( * ) Notice: Subject to any disclaimer, the term of this patent is extended or adjusted under 35 U.S.C. 154(b) by 265 days.

(21) Appl. No.: 11/721,896

(22) PCT Filed: Jul. 15, 2005

(86) PCT No.: PCT/IB2005/002029

§ 371 (c)(1),
(2), (4) Date: Mar. 13, 2008

(87) PCT Pub. No.: WO2006/064315

PCT Pub. Date: Jun. 22, 2006

(65) Prior Publication Data

US 2009/0134284 A1    May 28, 2009

(30) Foreign Application Priority Data

Dec. 17, 2004    (FR) .................................. 04 13472

(51) Int. Cl.
*B42F 13/00*    (2006.01)
(52) U.S. Cl. .................. 248/340; 248/97; 248/121; 248/125.8; 604/259
(58) Field of Classification Search .................. 248/95, 248/340, 97, 98, 176.1, 157, 125.1, 125.8, 248/176.3, 121; 5/600; 604/259, 257
See application file for complete search history.

(56) References Cited

U.S. PATENT DOCUMENTS

| 1,815,673 | A | | 7/1931 | Kelley |
| 3,177,870 | A | | 4/1965 | Salem, Jr. et al. |
| 4,191,297 | A | | 3/1980 | Hardman |
| 4,481,827 | A | | 11/1984 | Bilstad et al. |
| 4,559,036 | A | * | 12/1985 | Wunsch ........................ 604/81 |
| 4,585,436 | A | | 4/1986 | Davis et al. |
| 4,699,613 | A | * | 10/1987 | Donawick et al. ............. 604/80 |
| 4,852,641 | A | * | 8/1989 | Noble ........................ 165/80.1 |

(Continued)

FOREIGN PATENT DOCUMENTS

EP           0919475 A1    6/1999

(Continued)

*Primary Examiner*—Terrell Mckinnon
*Assistant Examiner*—Bradley H Duckworth
(74) *Attorney, Agent, or Firm*—Pearne & Gordon LLP

(57) ABSTRACT

The invention concerns a medical machine (1) for transport of liquid, comprising at least one suspension means (10) intended to receive at least two bags (50) containing liquid, the suspension means having a suspension body (11), at least three fastening means (12, 13, 14) fixed to the suspension body (11), comprising at least two lateral fastening means (13, 14) and one intermediate fastening means (12), the intermediate fastening means (12) being placed between the two lateral fastening means (13, 14), and the intermediate fastening means (12) being placed vertically lower down than the lateral fastening means (13, 14). The first lateral fastening means and the intermediate fastening means are intended to receive a first bag, and the second lateral fastening means and the intermediate fastening means are intended to receive a second bag, so that the two bags are held against one another in a stable manner.

24 Claims, 5 Drawing Sheets

U.S. PATENT DOCUMENTS

| | | |
|---|---|---|
| 5,000,407 A | 3/1991 | Juji et al. |
| 5,078,699 A | 1/1992 | Haber et al. |
| 5,094,418 A * | 3/1992 | McBarnes et al. ........ 248/286.1 |
| 5,137,158 A | 8/1992 | Brockway |
| 5,423,750 A | 6/1995 | Spiller |
| 5,609,572 A | 3/1997 | Lang |
| 5,722,947 A | 3/1998 | Jeppsson et al. |
| 5,820,086 A | 10/1998 | Hoffman et al. |
| 5,836,634 A | 11/1998 | Finkelman |
| 5,979,841 A | 11/1999 | Piraneo et al. |
| 6,264,035 B1 * | 7/2001 | Petrie ......................... 206/554 |
| 6,367,746 B1 | 4/2002 | Webb et al. |
| 6,390,311 B1 | 5/2002 | Belokin |
| 6,651,941 B1 | 11/2003 | Kinsel |
| 6,655,537 B1 * | 12/2003 | Lang et al. ............... 211/85.31 |

FOREIGN PATENT DOCUMENTS

| | | |
|---|---|---|
| FR | 2556300 A1 | 6/1985 |
| FR | 2756243 A1 | 5/1998 |
| FR | 2764270 A1 | 12/1998 |
| WO | 0193795 A2 | 12/2001 |
| WO | 0205875 A1 | 1/2002 |
| WO | 2004069312 A1 | 8/2004 |

* cited by examiner

MEDICAL MACHINE COMPRISING A SUSPENSION MEANS FOR SUSPENDING LIQUID BAGS

FIELD OF THE INVENTION

The invention concerns a medical machine for transport of liquid, comprising a suspension means for supporting bags containing liquid. This can be a machine for extracorporeal treatment of blood or for treatment of renal insufficiency or for receiving and storing liquid from a donor. The liquid can be treatment liquid to be withdrawn from the bag, or can be liquid taken from a patient or donor and to be introduced into the bag.

This invention is especially useful in the field of intensive care when a patient's kidneys suddenly no longer fulfill their function of purifying the blood. Medical personnel then have to very quickly initiate treatment with such a medical machine and they employ bags of treatment liquid which have been prepared in advance and are ready for use.

These treatment liquids are used in particular for purification or are injected directly into the patient, throughout the course of treatment. Therefore, these bags containing treatment liquid used on line have to be kept close to the machine during the treatment.

PRIOR ART

International application WO 2004/069312 filed in the name of the Applicant has disclosed a device for supporting containers in extracorporeal blood treatment machines, and a treatment machine comprising such a device. This application is incorporated herein by way of reference. The machine according to this prior art document is shown in FIGS. 1 and 1'. These illustrate a treatment machine 1 with a support device 2 arranged under the machine and intended to receive bags 3 in the lower space 4 of the machine.

This support device has at least one balance for weighing each bag of liquid used. This device also has a part capable of moving between two positions. The first is a non-operational loading position where the part is located outside the space delimited by the machine and permits easy loading or unloading of the bag. The second position is an operational treatment position in which the part is located within the lower space of the machine and supports the bag being used.

We now focus on the support 2 of this part, represented on its own in FIG. 2. The support 2 comprises a base body 6 formed by a bar, on which is fixed at least one hook 7 (three in the figure) for receiving the bag of treatment liquid which has the same number of holes as there are hooks, and a handle 8 allowing the support to be placed easily on the part described above.

The characteristics and advantages of the machine comprising such a support are as follows:

First, the operational position of use of the bag or bags is a position in which the bag is suspended in a stable manner inside the space defined by the machine and does not modify too much the position of the centre of gravity of the machine, so that the latter remains stable with the loaded bag or plurality of loaded bags.

Second, this support is used on a device intended to receive it and comprising at least one balance. This is because the volume of liquid used or infused during the treatment is monitored during the treatment and is used to control certain elements of the machine. In the case where several different liquids, and hence several differently filled bags, are used, it is necessary to have several balances placed in such a way that the respective bags do not touch one another and do not distort the weight measured by each balance.

Third, this support is used to place the bags of liquid in a lower space of the machine. Thus, the medical personnel do not have to lift relatively heavy bags of liquid up towards the top of the machine, as was usually required in the past. Thus, the device receiving this support is a device intended to receive the movable support already equipped with the bag. The user no longer has to arrange and fix the bag under the machine, and instead just has to fasten the bag initially to the support and then place the bar of the support equipped with the bag on the device. Ease of access is improved by this means.

This invention thus ensures stability of the loaded machine, correct measurement of the weights of each bag when at least two different bags of liquid are used, and ease of access for positioning of the bags.

However, these bags of treatment liquid have a capacity that can vary between 2 liters and 5 liters approximately, although bags with a capacity equal to 5 liters are very often used. The intensive treatment may last for several hours or several days and the members of the medical personnel must therefore replace the bags of liquid once they have run empty or are almost empty. This necessitates shutdown of the treatment by the machine, and sometimes also the shutdown of the extracorporeal blood circulation. The nurse has to clamp the access line of the bag, disconnect the bag, remove it from the machine, put an unused bag in place, connect it up and resume the treatment, checking that no anomaly has arisen. This takes several minutes, lengthens the period of treatment of the patient and requires the intervention of trained medical personnel.

The problem set by the present invention is thus that of limiting the changing of bags of treatment liquid, while at the same time maintaining stability of the loaded machine.

An additional problem, in the case where at least two different treatment liquids are used, is that of maintaining the same quality of measurement of the weight of each liquid used.

Another problem will be that of providing the user with easy access to the support in order to load and unload the treatment bags.

DISCLOSURE OF THE INVENTION

According to the invention, in order to achieve this object, a medical machine 1 is provided for transport of liquid, comprising at least one suspension means 10 intended to receive at least two bags 50 containing liquid, the suspension means having a suspension body 11, at least three fastening means (12, 13, 14) fixed to the suspension body 11, comprising at least two lateral fastening means (13, 14) and one intermediate fastening means 12, the intermediate fastening means 12 being placed between the two lateral fastening means (13, 14), and the intermediate fastening means 12 being placed vertically lower down than the lateral fastening means (13, 14).

Consequently the first lateral fastening means 13 and the intermediate fastening means 12 are intended to receive a first bag, and the second lateral fastening means 14 and the intermediate fastening means 12 are intended to receive a second bag. Thus, the invention makes it possible to use twice as many bags of treatment liquid, these bags being stored in a manner taking up only limited space because they are suspended and held against one another and are kept stable throughout treatment.

Other advantages and characteristics of the invention will become clear from reading the following description.

BRIEF DESCRIPTION OF THE DRAWINGS

Reference will be made to the attached drawings, in which:

FIG. 1 shows the whole of the treatment machine; FIG. 1' shows the bottom of this machine.

FIG. 10 shows the whole of the treatment machine; FIG. 11 shows the bottom of this machine.

The invention relates to the treatment machine, but, for better understanding, the suspension means belonging thereto has often been represented on its own, because it is not properly visible once placed on the machine.

Figure 1:
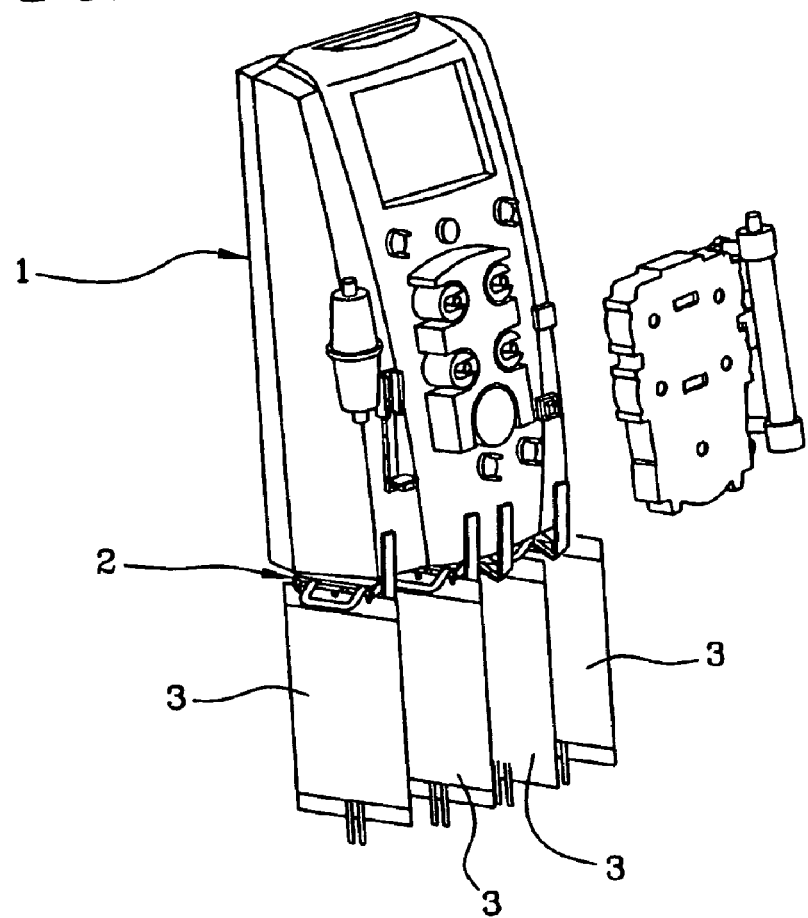
FIGS. 1, 1' and 2 illustrate a treatment machine according to the prior art.
Figure 1:
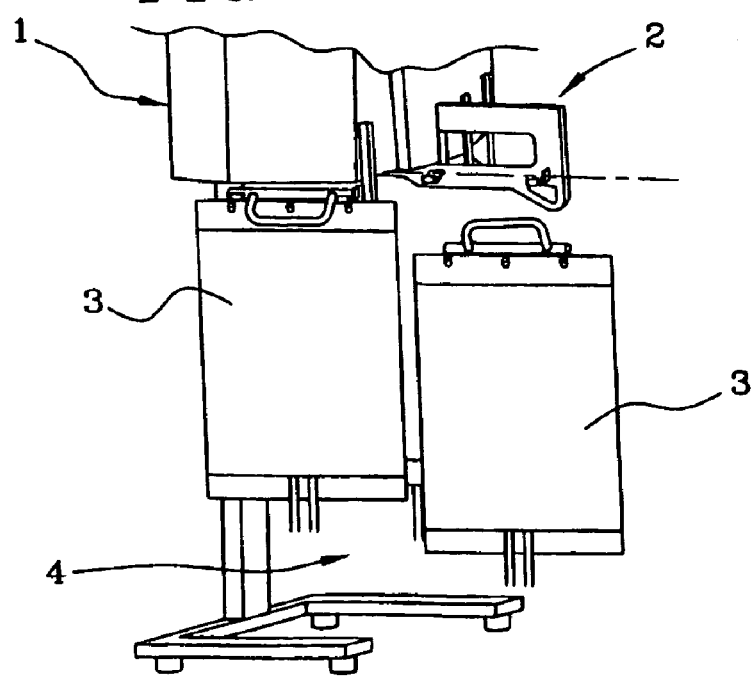
Figure 2:
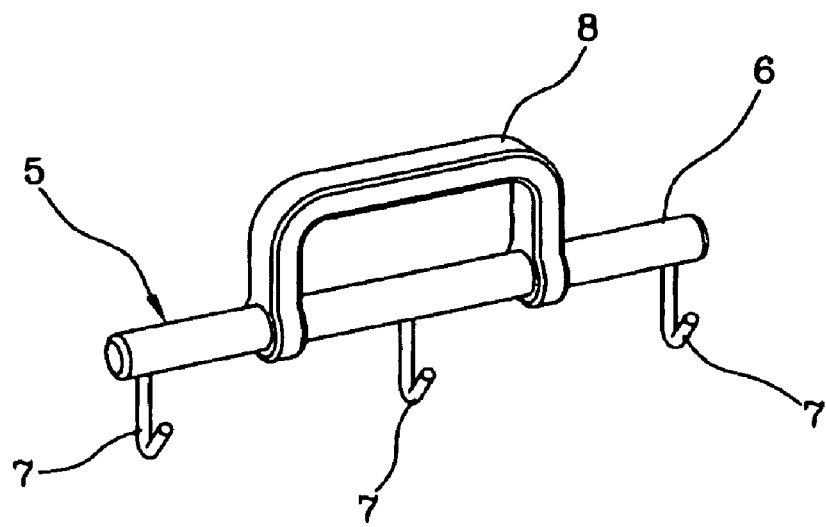
FIG. 2 shows a support device intended to be used on the treatment machine.
Figure 3:
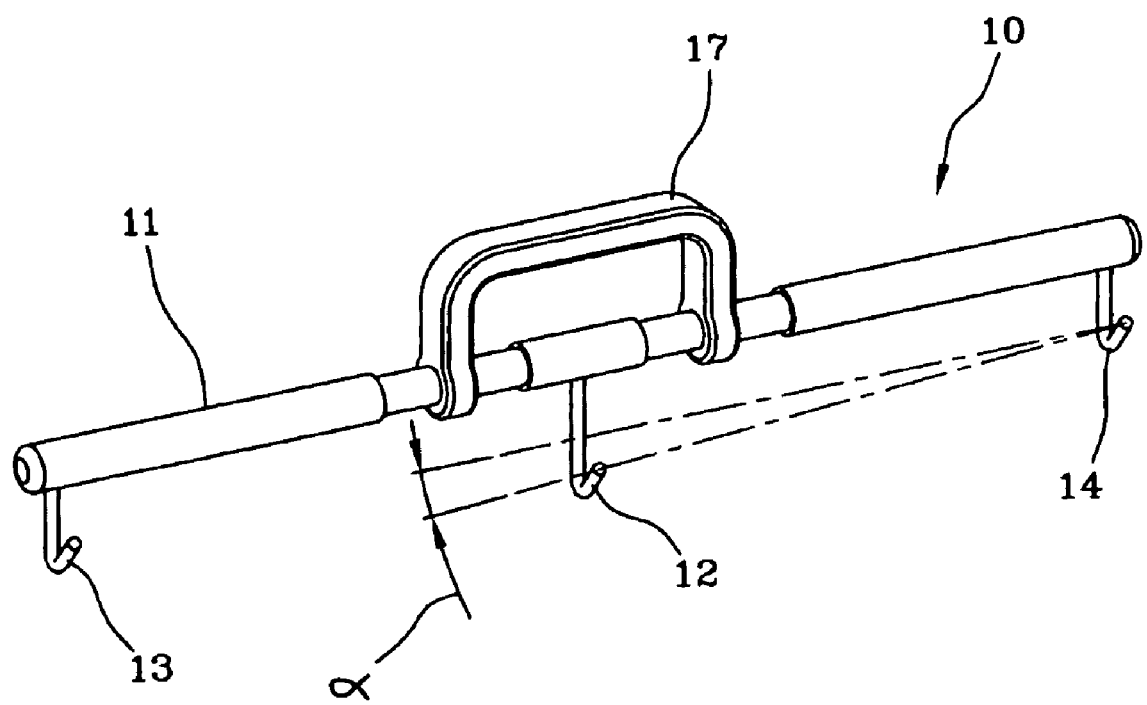
FIGS. 3 and 4 show a first embodiment of the suspension means intended to be used on the machine according to the invention.

FIG. 3 shows a suspension means 10 intended to receive at least two bags 50 containing liquid in accordance with the invention. The bags intended to contain fluid are flexible bags made of plastic, for example of PVC, and have substantially the shape of a rectangle. The suspension means 10 has a suspension body 11, at least three fastening means (12, 13, 14) fixed to the suspension body, of which an intermediate fastening means 12 is placed between the two lateral fastening means (13, 14). The intermediate fastening means 12 is placed vertically lower down than the lateral fastening means (13, 14).

Figure 10:
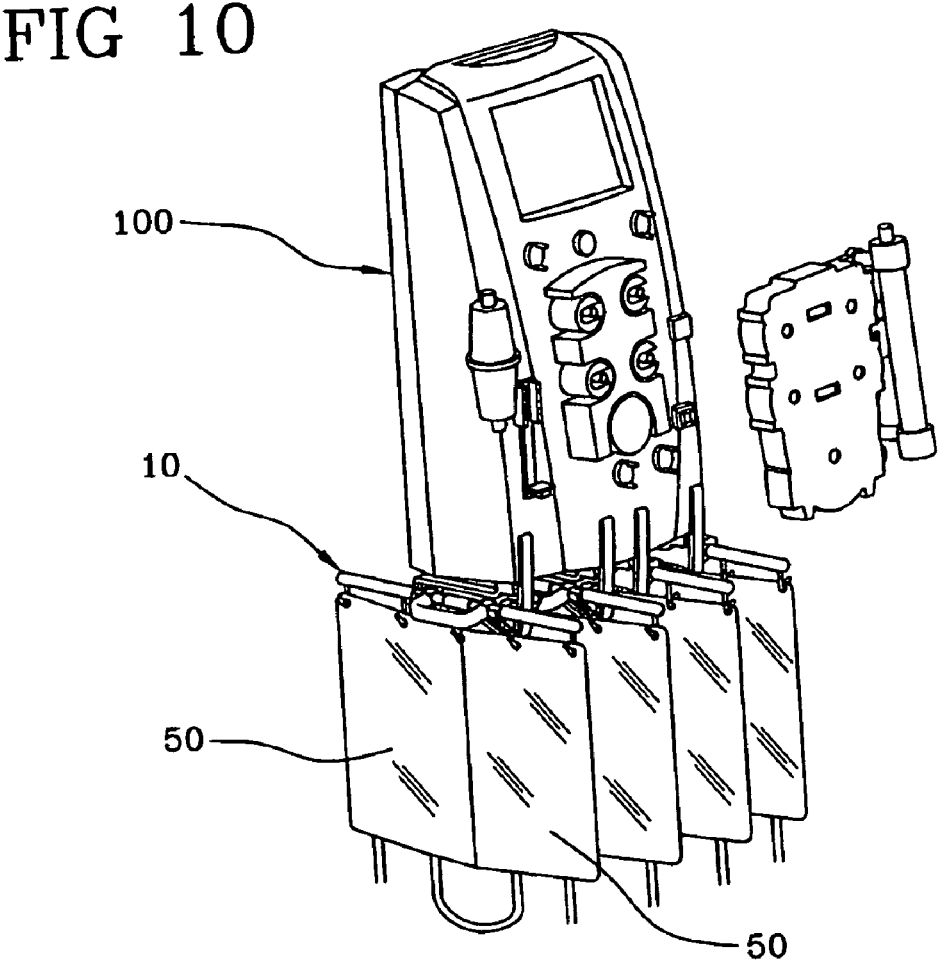
FIGS. 10 and 11 show a treatment machine according to the invention.
Figure 11:
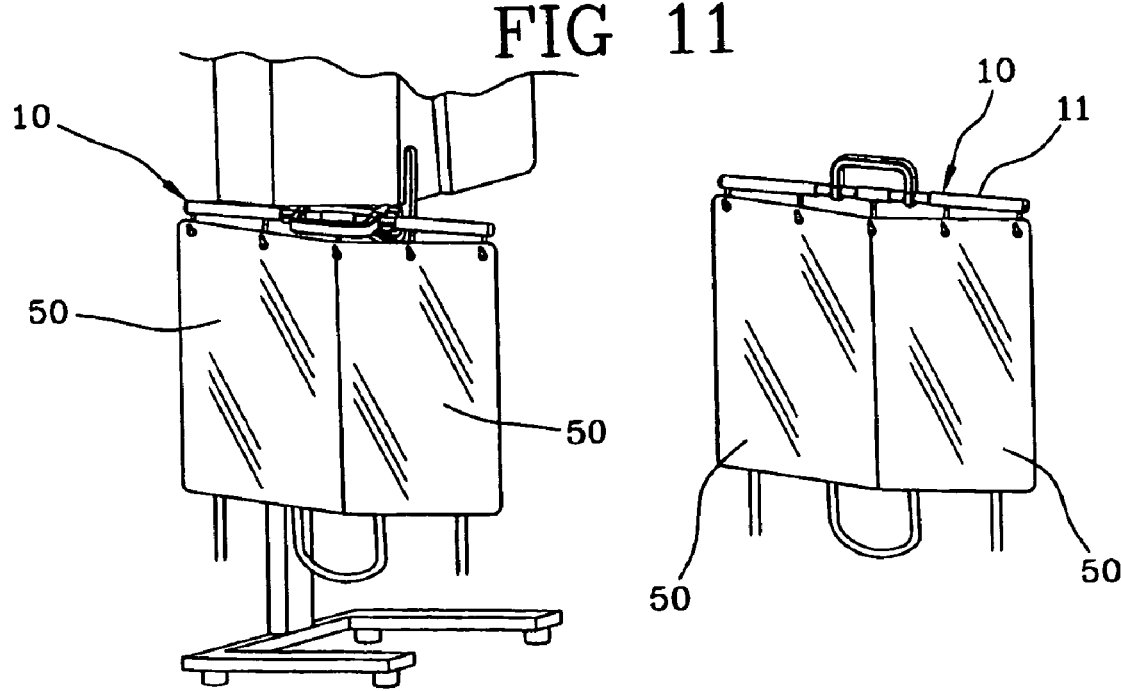

A first lateral fastening means 13 and the intermediate fastening means 12 are intended to receive a first bag, and the second lateral fastening means 14 and the intermediate fastening means 12 are intended to receive a second bag. The position of the intermediate fastening means 12 supporting the two bags is such that the two bags are held against one another on account of their weight, as is illustrated in FIGS. 10 and 11. The two bags used are placed at the same height and with the same inclination and empty at the same speed.

Figure 8:
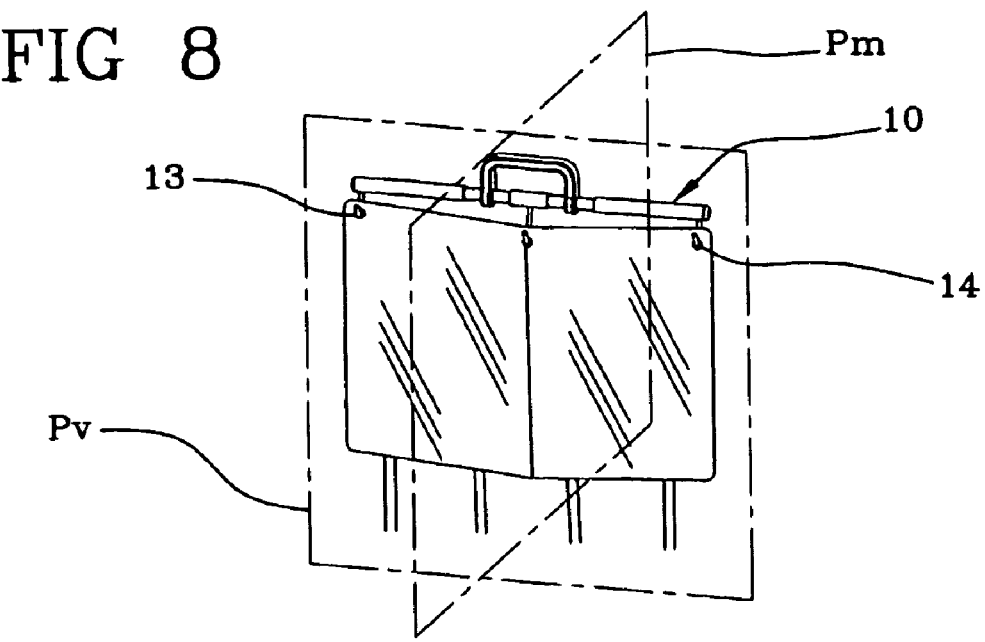
FIGS. 8 and 9 show the spatial arrangement of the first embodiment of the suspension means intended to be used on the machine according to the invention, singly or in combination.

The intermediate fastening means 12 is placed substantially on the median plane (Pm) of the two lateral fastening means (13, 14), as is illustrated in FIG. 8: this allows two identical bags to remain perfectly against one another throughout the course of treatment.

The lateral fastening means (13, 14) can be terminal fastening means: they are consequently placed on the ends of the suspension body 11.

The lateral fastening means can be placed vertically at the same height.

Each of the fastening means (12, 13, 14) has at least one fastening point. By fastening point, we mean a precise point at which a part of the bag will be suspended. Each fastening point (12, 12', 12", 13, 14) is chosen from a group comprising clips, hooks or other equivalent means employed by the skilled person. The figures show a hook, but any means capable of being used by the skilled person to ensure a suspension function can be used.

Figure 5:
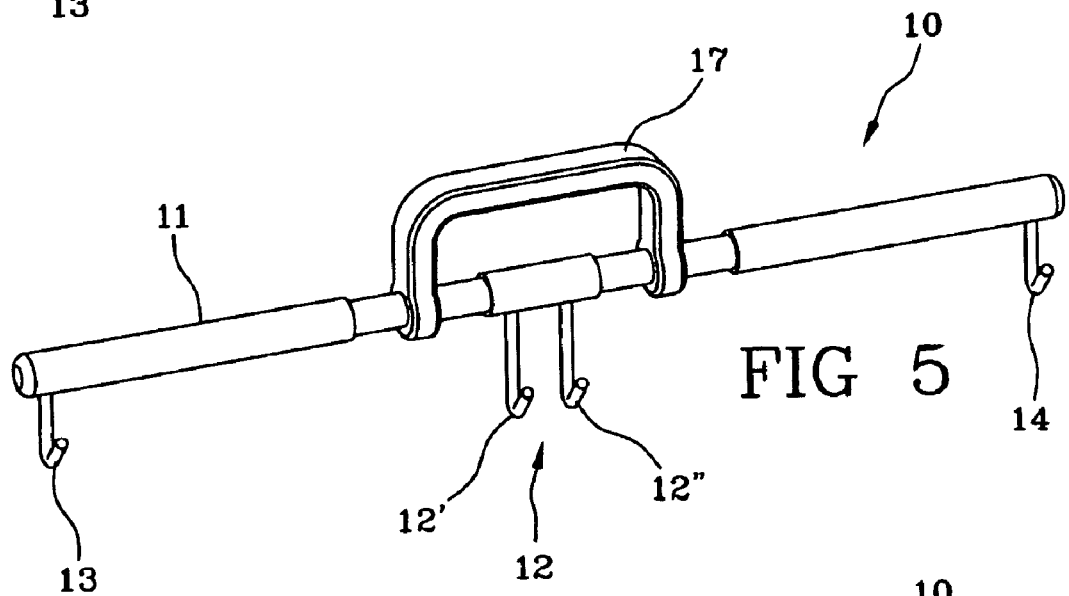
FIGS. 5 and 6 show a second embodiment of the suspension means intended to be used on the machine according to the invention.

The intermediate fastening means 12 can have two fastening points (12', 12") arranged vertically at the same height, as is illustrated in FIG. 5. A first bag will be suspended from a first intermediate fastening point 12' and from the nearest lateral fastening point; and the second bag, identical to the first in this illustration, will be suspended from the second intermediate fastening point 12" and from the fastening point nearest to it. The two intermediate fastening points 12' and 12" will be relatively close to one another so that the bags remain held against one another.

The degree of inclination of each bag will be defined by the angle $\alpha$ formed by the horizontal and the straight line connecting one of the lateral fastening means (13, 14) and the intermediate fastening means (12), as is shown in FIG. 3.

Figure 6:
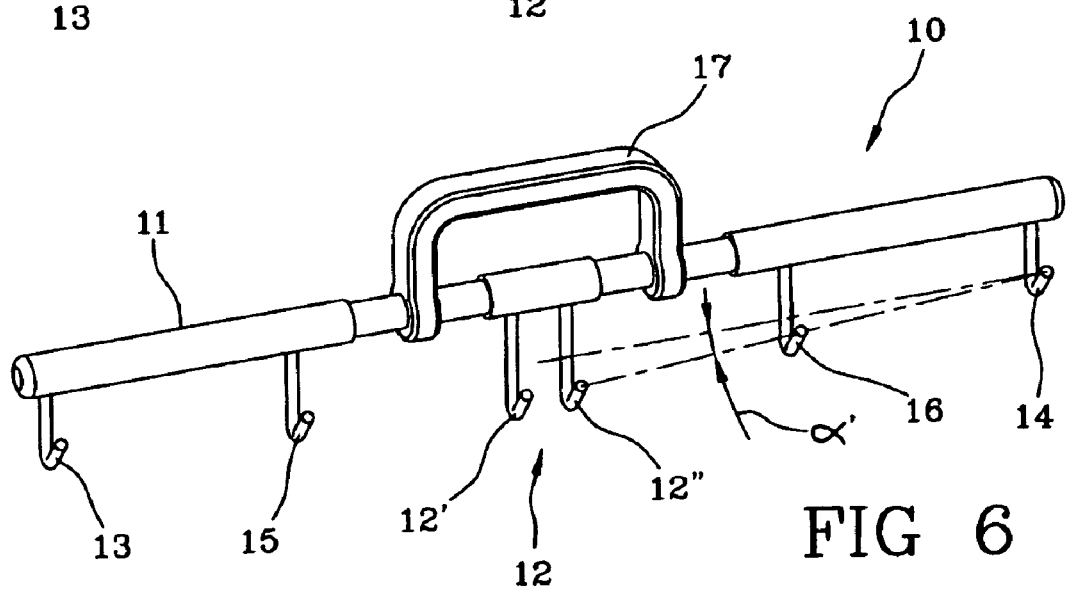

Similarly, in the case where the intermediate fastening means comprises two fastening points, it is the angle $\alpha'$ formed by the horizontal and the straight line connecting one of the lateral fastening means (13, 14) and the fastening point of the intermediate fastening means (12', 12") nearest to the lateral means that will define the inclination of each bag, as is shown in FIG. 6.

The angle $\alpha$ or $\alpha'$ is between 2 and 25 degrees. More precisely, the angle $\alpha$ or $\alpha'$ used is less than 15°, but greater than 2°. In a particular embodiment, the angle $\alpha$ or $\alpha'$ is substantially equal to 5°.

Figure 4:
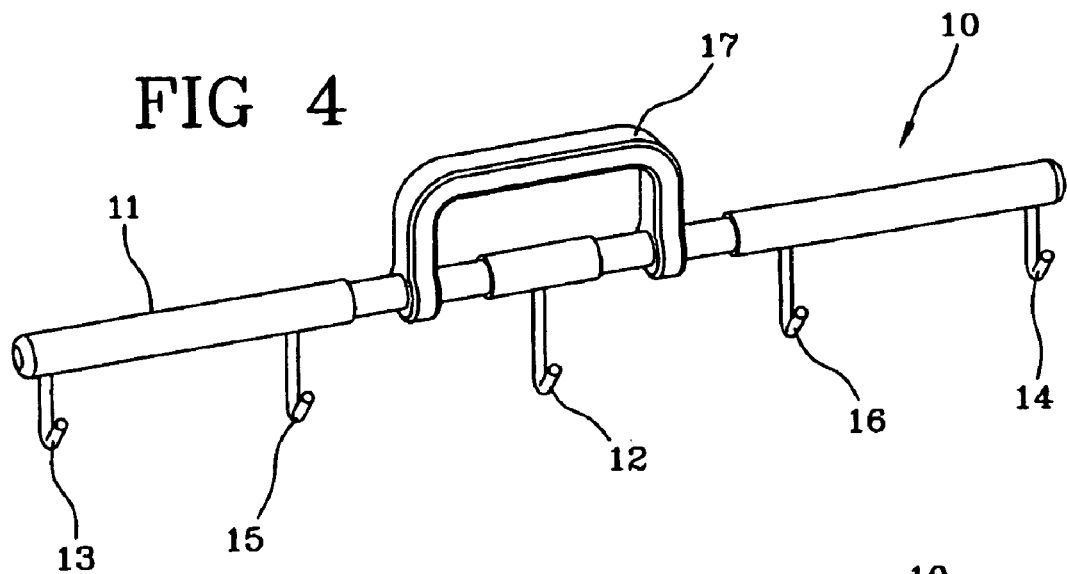

The suspension means can comprise at least one additional fastening means (15, 16) fixed on the suspension body 11 on each segment connecting one of the two lateral fastening means (13, 14) to the intermediate fastening means 12. This additional fastening means, which can be a clip or a hook or equivalent, makes it possible to strengthen the stability of each bag in its inclined position and in a well-defined plane. Whatever the content of the bag at any given moment during treatment, the flexible bag will not be deformed. It will be appreciated that each additional fastening means (15, 16) can be placed substantially at the middle of said segment, as is illustrated in FIGS. 4 and 6.

Figure 7:
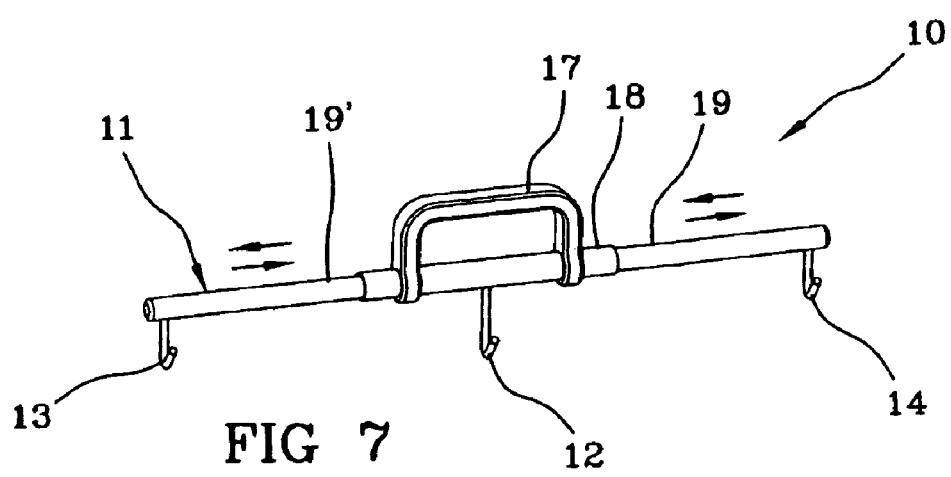
FIG. 7 shows a third embodiment of the suspension means intended to be used on the machine according to the invention.

The suspension means 10 can furthermore have a telescopic structure (18, 19, 19'), as is shown in FIG. 7. In this case, the suspension body 11 has a first structure 18 fixed relative to the machine, and a second, movable structure (19, 19') with a first part 19 and a second part 19' which are placed each side of the first structure 18 and both slide inside the first structure 18. This makes it possible to change from a "retracted" state for storage to an "extended" state for use and also makes it possible to adapt the suspension means 10 to the size of the bag (for example if dips are used) or of holes in the bag (for example if hooks are used).

In a particular embodiment, the three fastening means (12, 13, 14) of the suspension means 10 are coplanar and in a vertical plane (Pv). Thus, the two bags will be suspended in a stable manner and held against one another in the same plane Pv, as is shown in FIG. 8.

Figure 9:
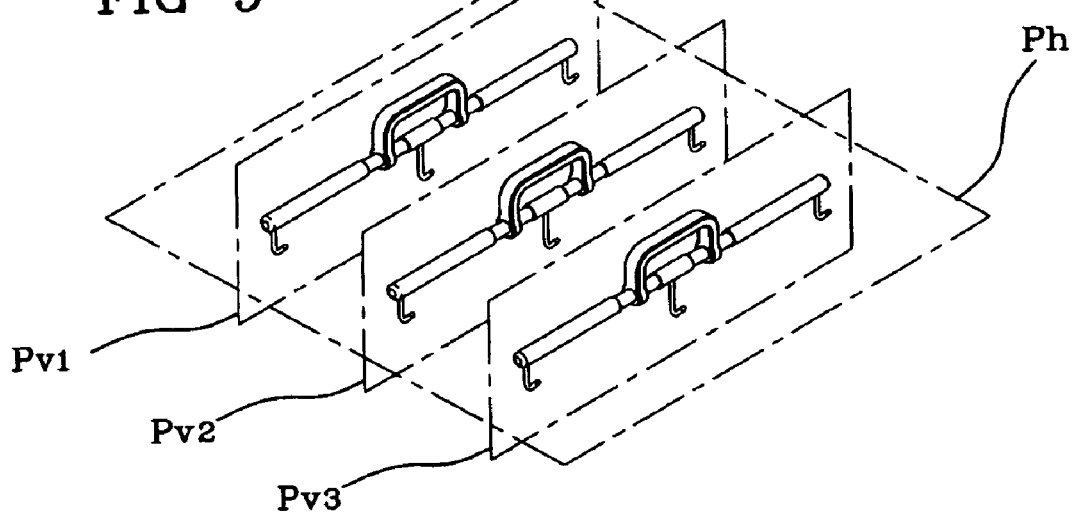

This configuration is effective when several different bags of fluid are to be used and weighed during the treatment. The machine will comprise at least two identical suspension means 10 which are fixed to the machine and placed in parallel planes (Pv1, Pv2, Pv3), as is shown in FIG. 9. The two means will be at a sufficient distance from one another to ensure that the suspended pairs of bags do not touch one another and do not distort the weight measurement.

Additionally, the lateral fastening means (13, 14) of each suspension means 10 are all coplanar in the same horizontal plane (Ph): the bags will be aligned at the same height. This configuration makes it possible to reduce to a minimum the space needed for storage of the bags. The bags suspended in pairs do of course take up more room than a single bag, but they take up a minimum amount of additional space. As the bags empty, the weight of the inclined bags held against one another will be such that the liquid, inside the bag, will always be brought towards the vertical median axis of the suspension means, so taking up less and less space on the sides of the machine.

Moreover, the suspension means 10 according to the invention can be removable from the treatment machine and can have a grip element 17, a handle for example or any other known equivalent means, for engaging the suspension means on the machine and disengaging the suspension means from the machine. This makes it easier to fit the bags on the machine and to remove them from the machine, especially since the weight of the liquid will be doubled. It will be a simple matter for the medical personnel to fit the pair of bags on the suspension means and then place said means on the machine.

Thus, during its operation, the machine will have at least one suspension means on which there will be suspended two identical bags containing treatment liquid and being able to be brought into fluidic communication with one another. The first bag will be fastened on the one hand to one of the two lateral fastening means 13 and on the other hand to the intermediate fastening means 15, and the second is bag will be fastened on the one hand to the intermediate fastening means 15 and on the other hand to the other lateral fastening means 14 so that the two bags are held against one another in a stable manner. The machine will have at least two identical suspension means 10 which are placed in two vertical parallel planes and to each of which will be fastened a pair of bags containing treatment liquid and being able to be brought into fluidic communication.

The bags could be fastened to the suspension means when placed in the lower space of the machine, as is shown in FIGS. 10 and 11.

ADVANTAGES OF THE INVENTION

The present invention affords numerous advantages:
the stability of the pair of suspended bags at any moment during treatment and at any level of filling of the bags;
in the case where at least two treatment liquids have to be used and weighed separately: the stability of the plurality of pairs of bags and the quality of measurement of the weights of the bags;
the stability of the machine resulting from the placement of the bags in the lower space of the machine;
the ease of access for loading and unloading the bags by virtue of the removability of the suspension device;
the simplicity and low cost of production of the suspension means which can be used on the machine as described in this application or in application WO 2004/069312 or in any other medical machine for transport of fluid;
the adaptability of the suspension device to the size and volume of the bags used, by virtue of its telescopic structure;
the time lost in replacing bags is halved, resulting in time savings for the medical personnel and in improved continuity of treatment of the patient;
the amount of space taken up by the pairs of bags is reduced to a minimum by their being held against one another, and their shape changes so as to bring the remaining liquid towards the median axis of the suspension means;
there will be less likelihood of the medical personnel touching the bags when moving around the machine.

The invention claimed is:

1. A medical machine for transport of liquid, comprising an upper unit (100) which can transport liquid and at least two suspension means (10), each suspension means (10) being configured and located so that at least a first bag containing liquid and a second bag containing liquid can be suspended therefrom and being configured and located so that said first and second bags can be located (1) in a lower space of the medical machine, (2) vertically lower than the upper unit, or (3) substantially beneath the upper unit, the two suspension means being located in parallel planes, each suspension means having:
   a suspension body (11),
   at least three fastening means (12, 13, 14) fixed to the suspension body (11), comprising a first lateral fastening means (13), a second lateral fastening means (14) and one intermediate fastening means (12), the intermediate fastening means (12) being placed between the two lateral fastening means (13, 14), and vertically lower down than each of the lateral fastening means (13, 14), the first lateral fastening means (13) and the intermediate fastening means (12) being configured so that the first bag can be hung from the first lateral fastening means (13) and the intermediate fastening means (12), and the second lateral fastening means (14) and the intermediate fastening means (12) being configured so that the second bag can be hung from the second lateral fastening means (14) and the intermediate fastening means (12) an angle $\alpha$ being defined by a horizontal line and a straight line connecting one of the lateral fastening means (13, 14) and the intermediate fastening means (12).

2. Machine according to claim 1, where the intermediate fastening means (12) is placed substantially on a median plane (Pm) of the two lateral fastening means (13, 14).

3. Machine according to claim 1, where the lateral fastening means (13, 14) are terminal fastening means.

4. Machine according to claim 1, where the lateral fastening means are placed vertically at the same height.

5. Machine according to claim 1, where each of the fastening means (12, 13, 14) has at least one fastening point.

6. Machine according to claim 1, where the intermediate fastening means (12) has two fastening points (12', 12") arranged vertically at the same height.

7. Machine according to claim 5, where each said fastening point is chosen from among a group including clips and hooks.

8. Machine according to claim 1, where the angle $\alpha$ formed by the horizontal and the straight line connecting one of the lateral fastening means (13, 14) and the intermediate fastening means (12) is between 2 and 25 degrees.

9. Machine according to claim 6, where an angle $\alpha'$ formed by a horizontal line and a straight line connecting one of the lateral fastening means (13, 14) and the fastening point of the intermediate fastening means (12', 12") nearest to a lateral means is between 2 and 25 degrees.

10. Machine according to claim 8, where the angle $\alpha$ is less than 15°.

11. Machine according to claim 10, where the angle $\alpha$ is substantially equal to 5°.

12. Machine according to claim 1, where at least one additional fastening means (15, 16) is fixed on the suspension body (11) on each segment connecting one of the two lateral fastening means (13, 14) to the intermediate fastening means (12).

13. Machine according to claim 12, where each additional fastening means (15, 16) is placed substantially on the middle of said segment.

14. Machine according to claim 1, where at least one suspension means (10) has a telescopic structure (18, 19, 19').

15. Machine according to claim 14, where the suspension body (11) has a first structure (18) fixed relative to the machine and a second, movable structure (19, 19') with a first part (19) and a second part (19') which are placed on each side of the first structure (18) and both slide inside the first structure (18).

16. Machine according to claim 1, where the three fastening means (12, 13, 14) of the suspension body are coplanar in a vertical plane (Pv).

17. Machine according to claim 16, wherein the two suspension means (10) are fixed to the machine.

18. Machine according to claim 17, where the lateral fastening means (13, 14) of each suspension means (10) are all coplanar in the same horizontal plane (Ph).

19. Machine according to claim 1, where at least one suspension means (10) is removable from the machine and has a grip element (17) for engaging the suspension means (10) on the machine and disengaging the suspension means (10) from the machine.

20. Machine according to claim 1, having at least one suspension means (10) on which are suspended two identical bags containing liquid, the first bag being fastened on the one hand to one of the two lateral fastening means (13) and on the other hand to the intermediate fastening means (12), and the second bag being fastened on the one hand to the intermediate fastening means (12) and on the other hand to the other lateral fastening means (14), so that the two bags are held against one another.

21. Machine according to claim 20, wherein a pair of bags containing liquid is attached to each of the suspension means (10).

22. Machine according to claim 6, where each of said fastening points is chosen from among a group including clips and hooks.

23. Machine according to claim 9, where the angle $\alpha'$ is less than 15°.

24. Machine according to claim 23, where the angle $\alpha'$ is substantially equal to 5°.

\* \* \* \* \*